United States Patent [19]

Nash, Jr. et al.

[11] Patent Number: 4,969,993
[45] Date of Patent: Nov. 13, 1990

[54] CHROMATOGRAPHIC INSTRUMENT WITH COMMAND SEQUENCING

[75] Inventors: Thomas H. Nash, Jr., Easton; Celia P. Chang, New Canaan; Anthony F. Poile, Ridgefield, all of Conn.

[73] Assignee: The Perkin-Elmer Corporation, Norwalk, Conn.

[21] Appl. No.: 401,396

[22] Filed: Aug. 31, 1989

[51] Int. Cl.$^5$ ............................................. B01D 15/08
[52] U.S. Cl. ............................... 210/198.2; 73/61.1 C; 210/96.1; 210/143; 364/499; 364/502; 422/70
[58] Field of Search ...................... 73/61.1 C; 210/656, 210/96.1, 143, 198.2; 364/499, 502; 422/70; 436/161

[56] References Cited

U.S. PATENT DOCUMENTS

| | | | |
|---|---|---|---|
| 3,960,003 | 6/1976 | Beyer et al. | 73/61.1 C |
| 4,357,668 | 11/1982 | Schwartz et al. | 210/198.2 |
| 4,472,354 | 9/1984 | Passell et al. | 422/70 |
| 4,579,663 | 4/1986 | Poile et al. | 210/656 |
| 4,674,323 | 6/1987 | Rulf et al. | 422/70 |
| 4,802,981 | 2/1989 | Kenney et al. | 210/656 |

Primary Examiner—Peter Hruskoci
Attorney, Agent, or Firm—H. S. Ingham; E. T. Grimes

[57] ABSTRACT

A liquid chromatographic instrument includes specimen vessels in randomly designated locations. An automatic sampler sequentially samples specimens from selected vessels based on instructions from a set of command instruction lines. A detector module measures characteristics of each sampled specimen, and results for each test specimen relative to a standard specimen are computed. A command sequence program includes reading of a user inputed ordered list to effect a sequential selection of each location designation according to the ordered list, generation of a command instruction line corresponding to each sequential selection and containing a location designation and measurement instructions for each selected specimen, counting of the number of command instruction lines generated since a nearest prior calibration command instruction line, and in response to the counting number being equal to the calibration frequency, generation of a next calibration command instruction line containing the location designation and the measurement instructions for the standard specimen.

14 Claims, 14 Drawing Sheets

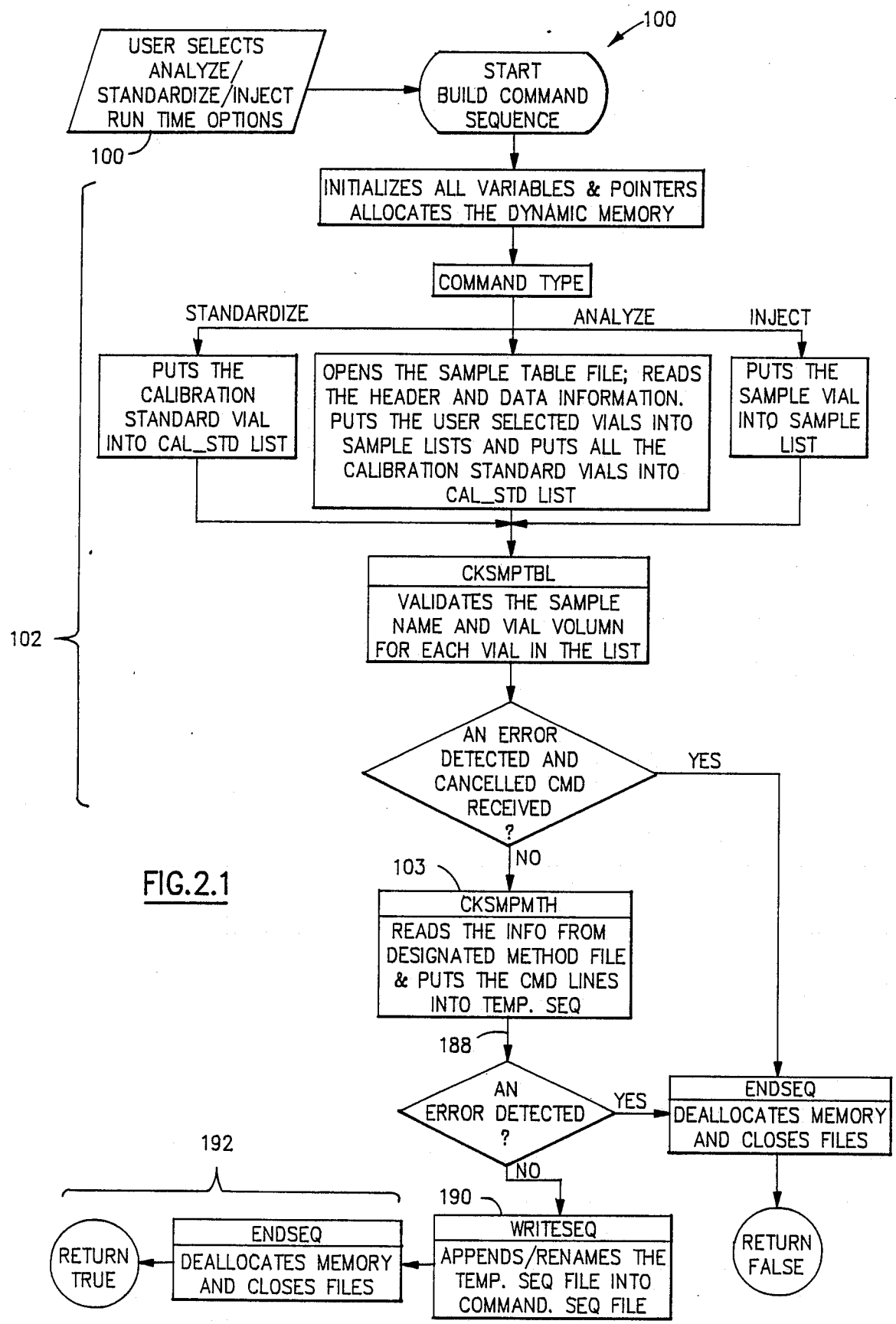
FIG.2.1

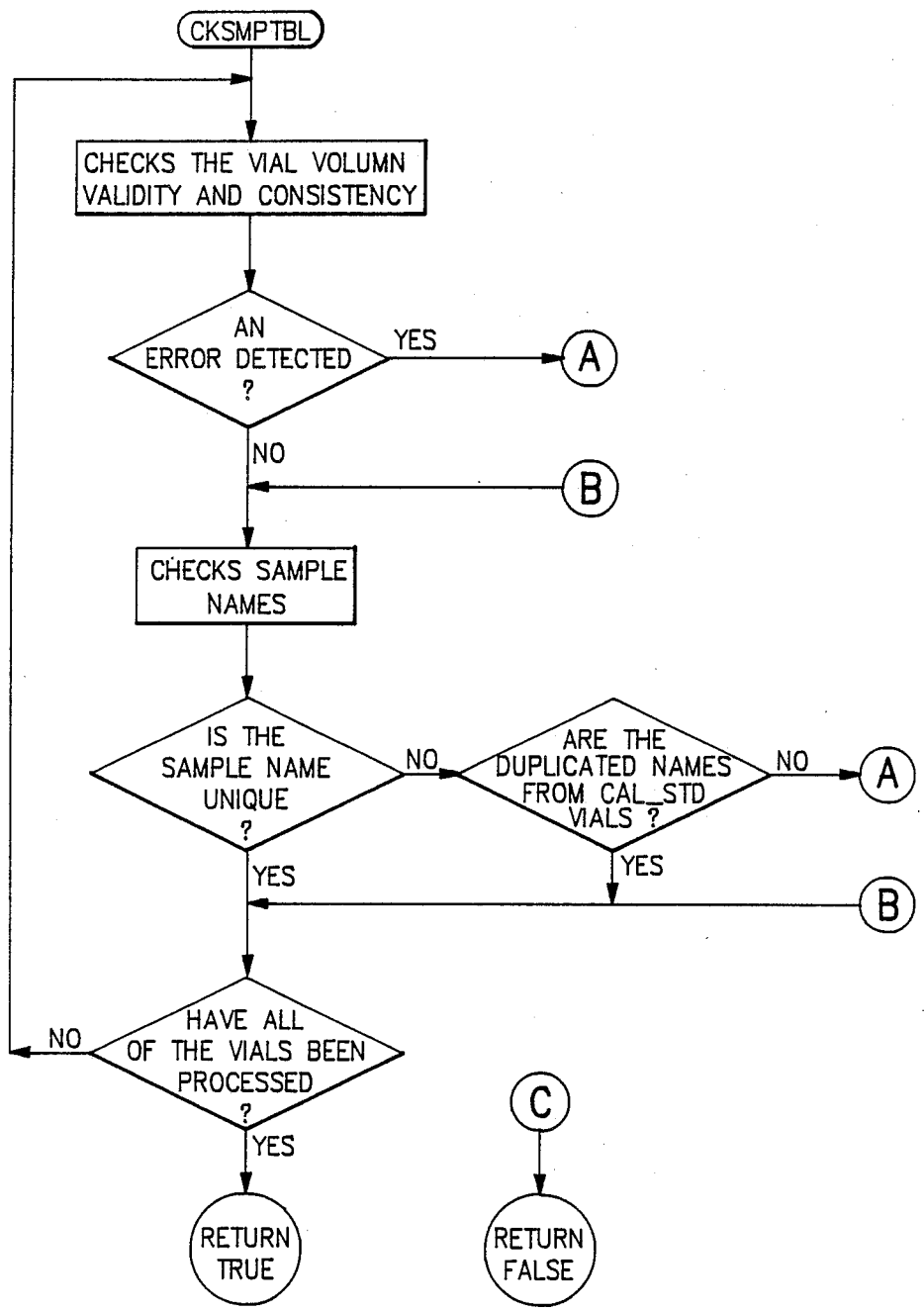
FIG.2.2

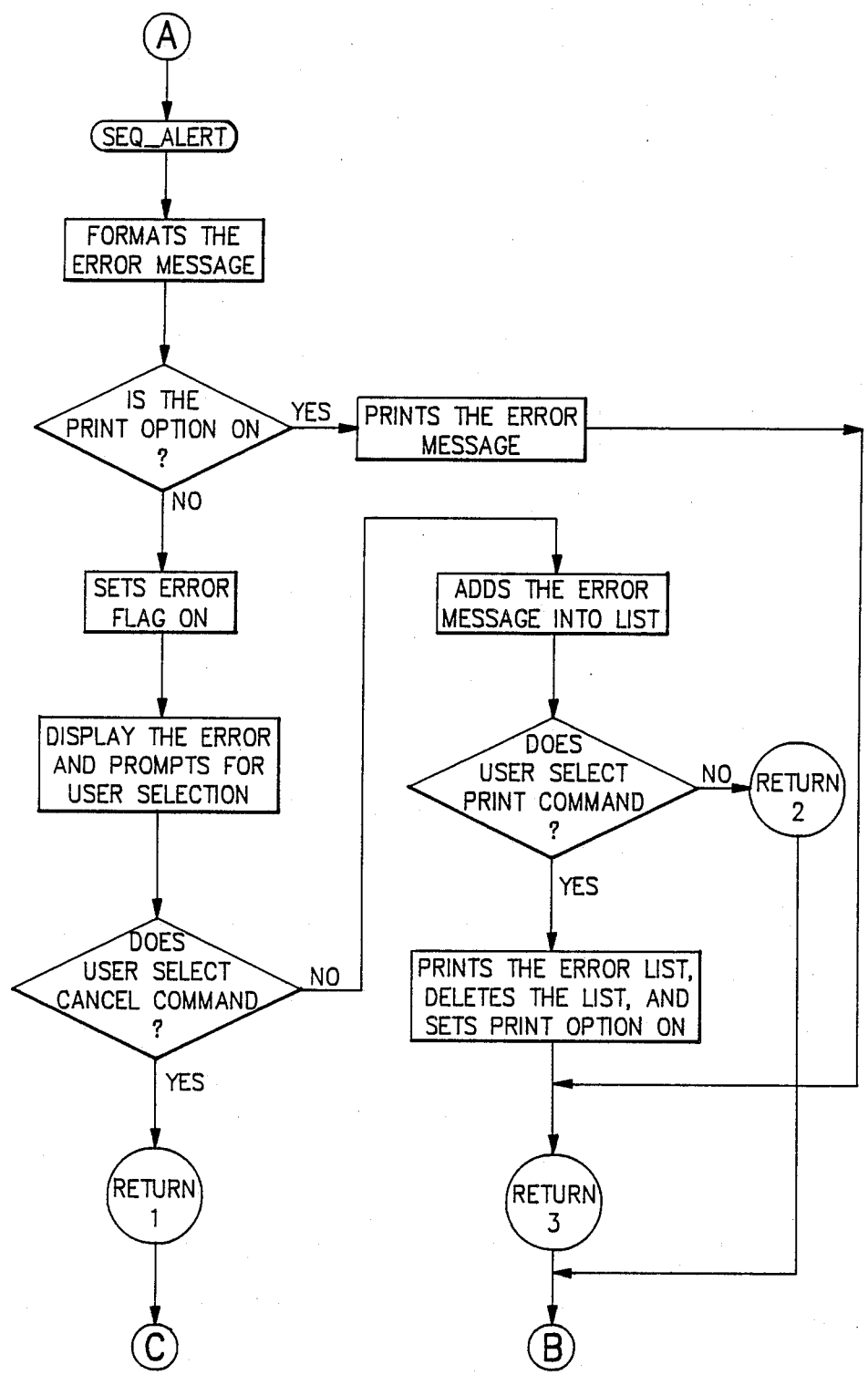
FIG.2.3

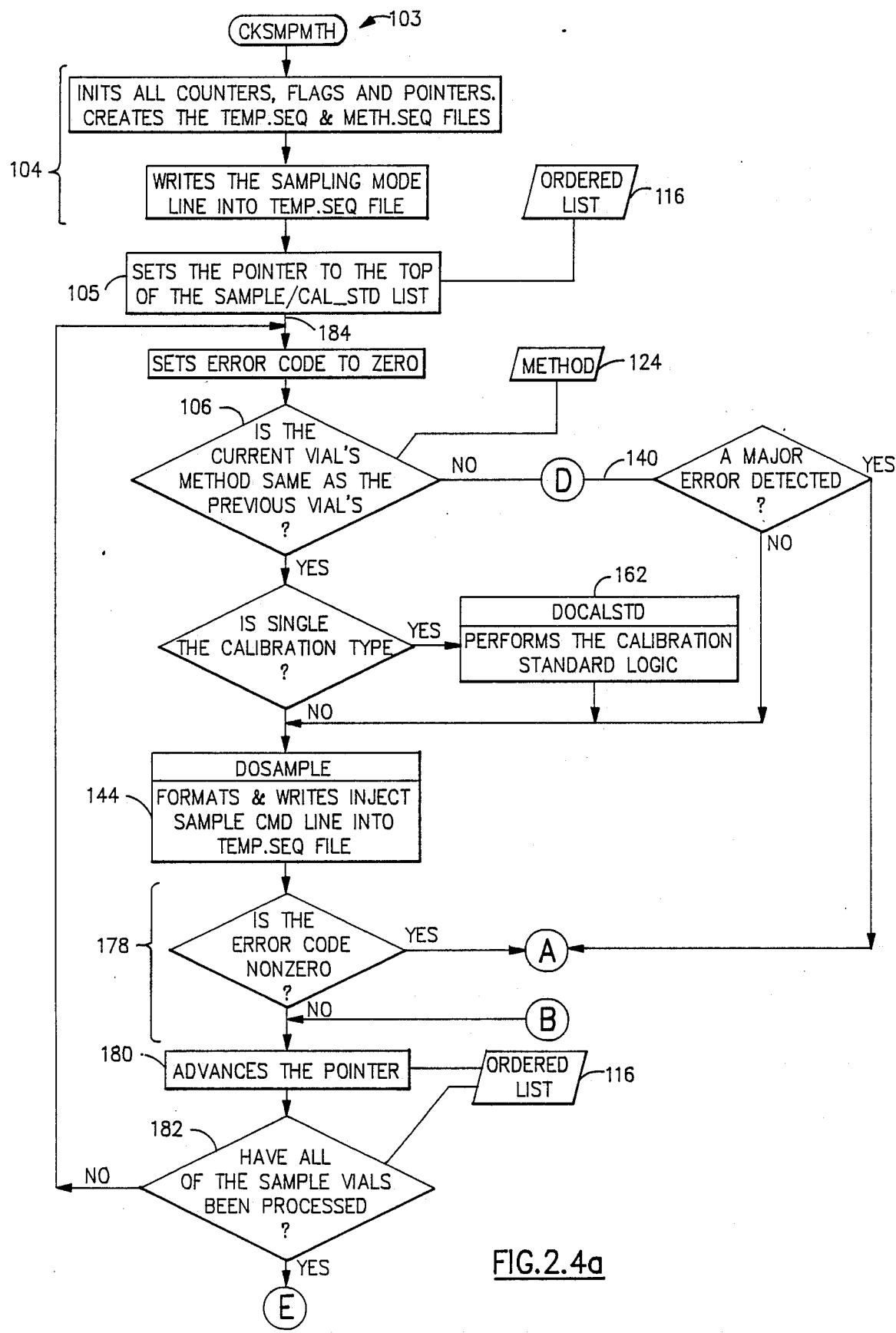
FIG.2.4a

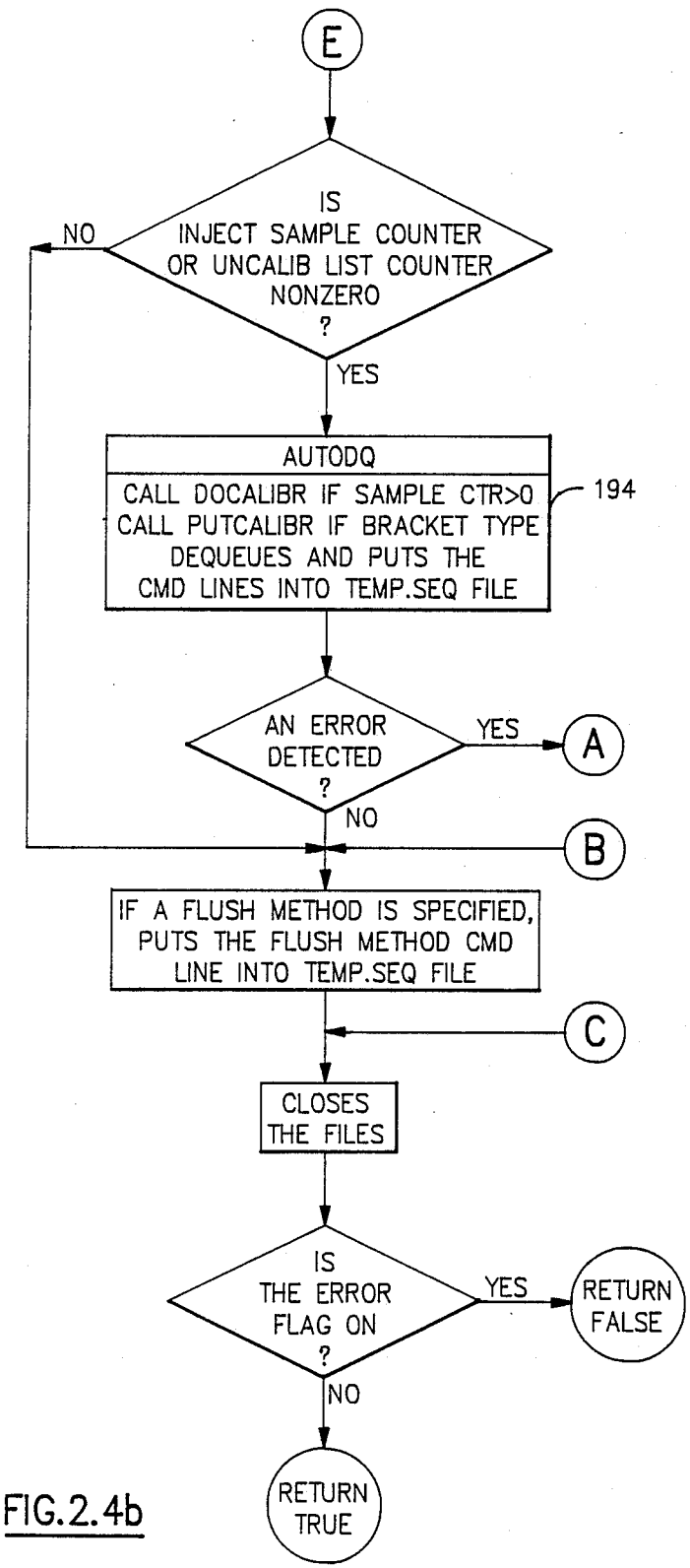
FIG.2.4b

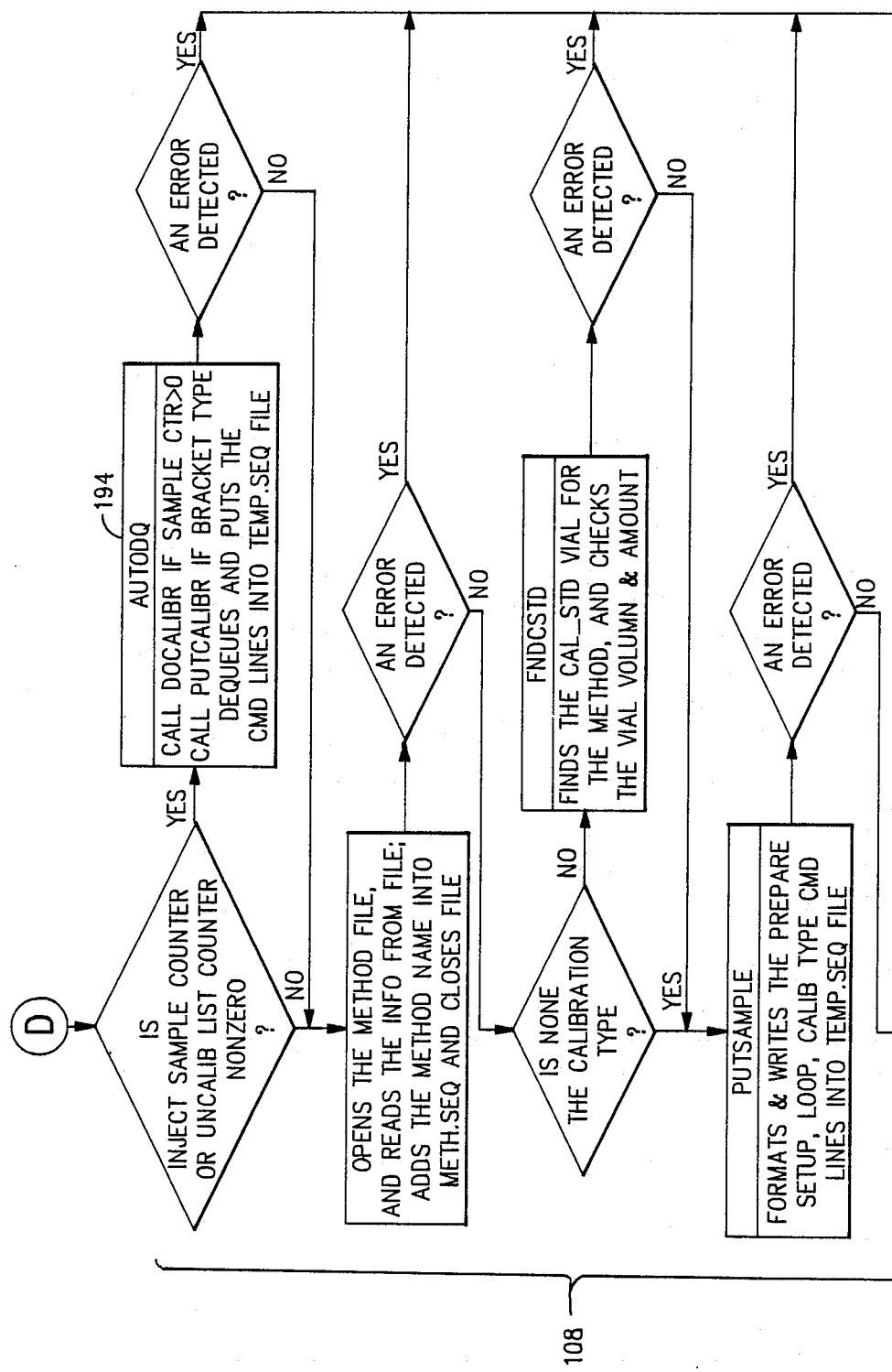
FIG.2.5a

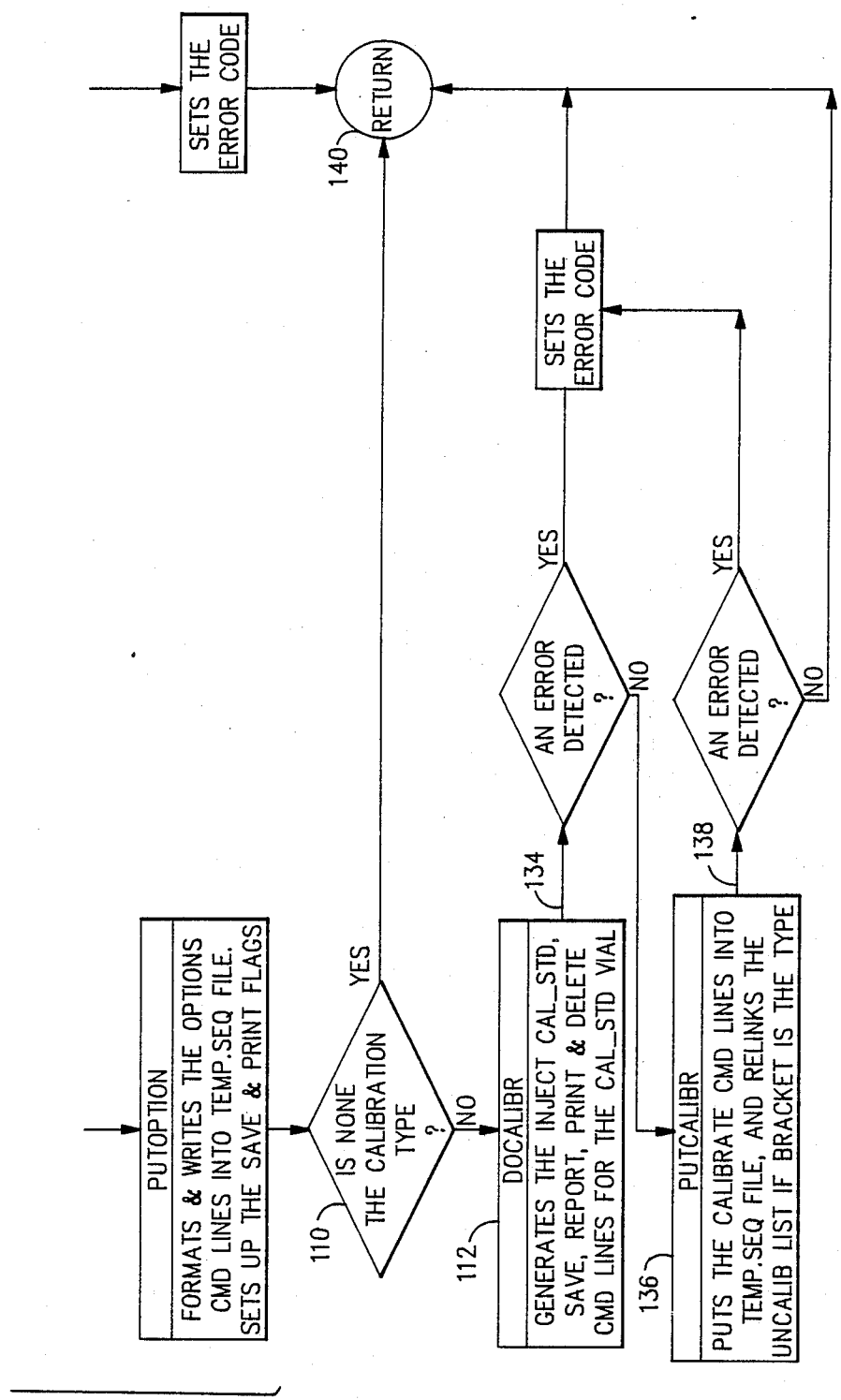

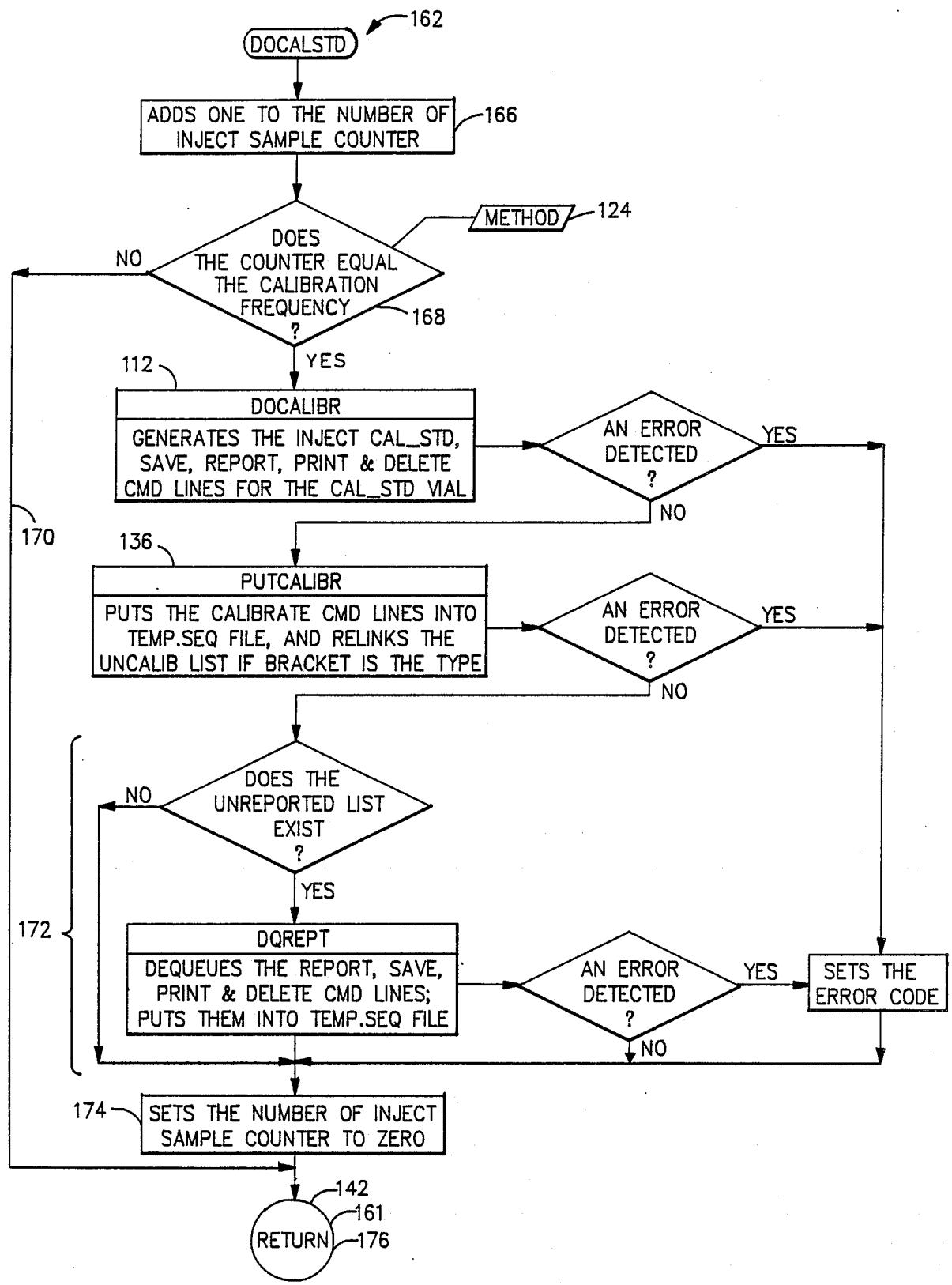
FIG.2.6

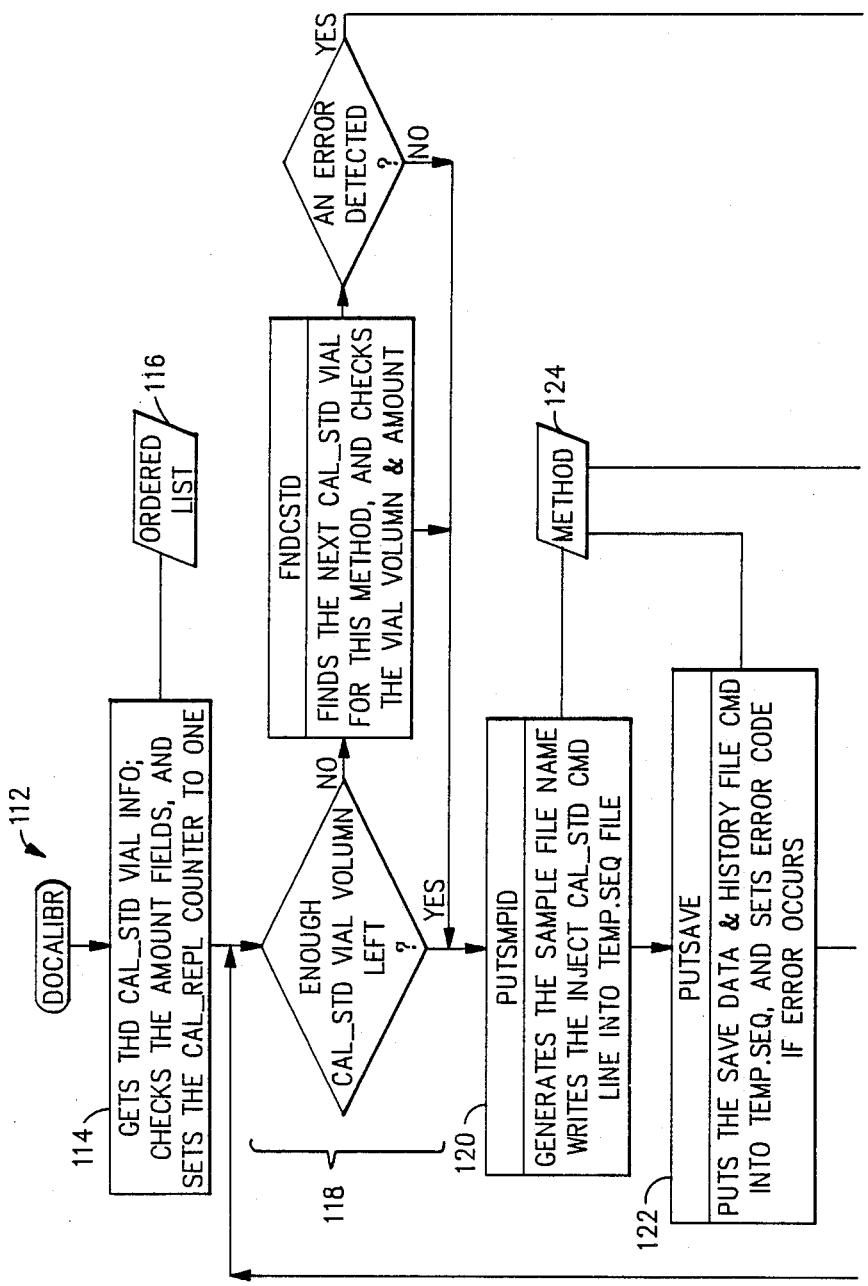
FIG 2.7a

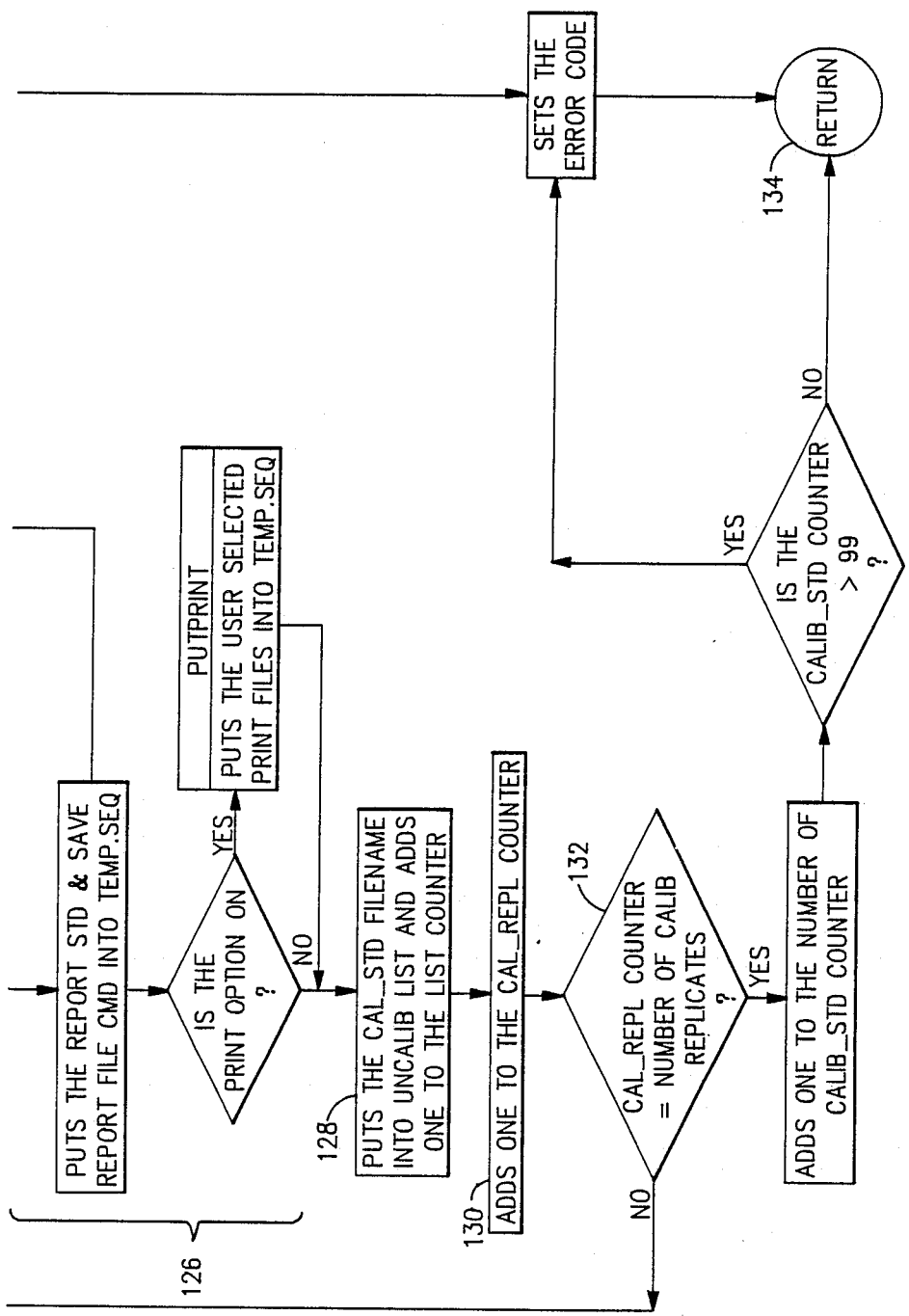
FIG.2.7b
FIG.2.7

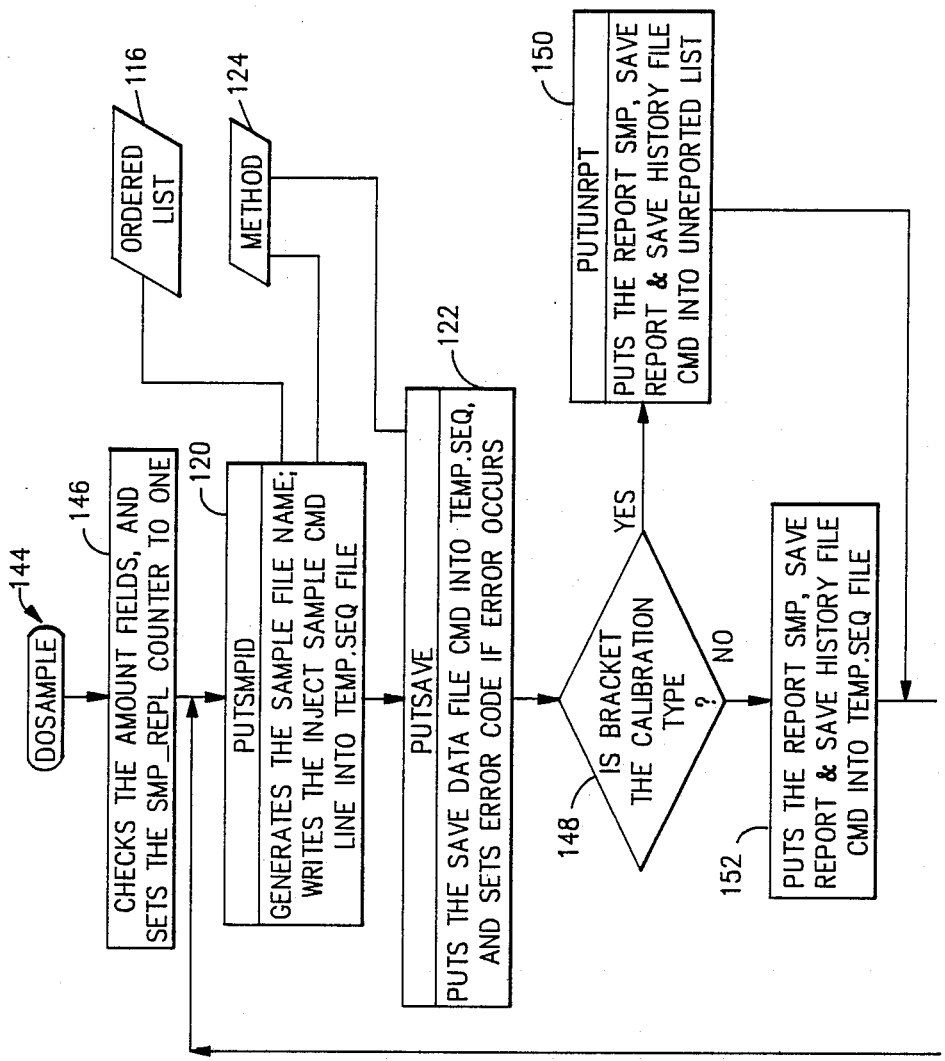
FIG.2.8a

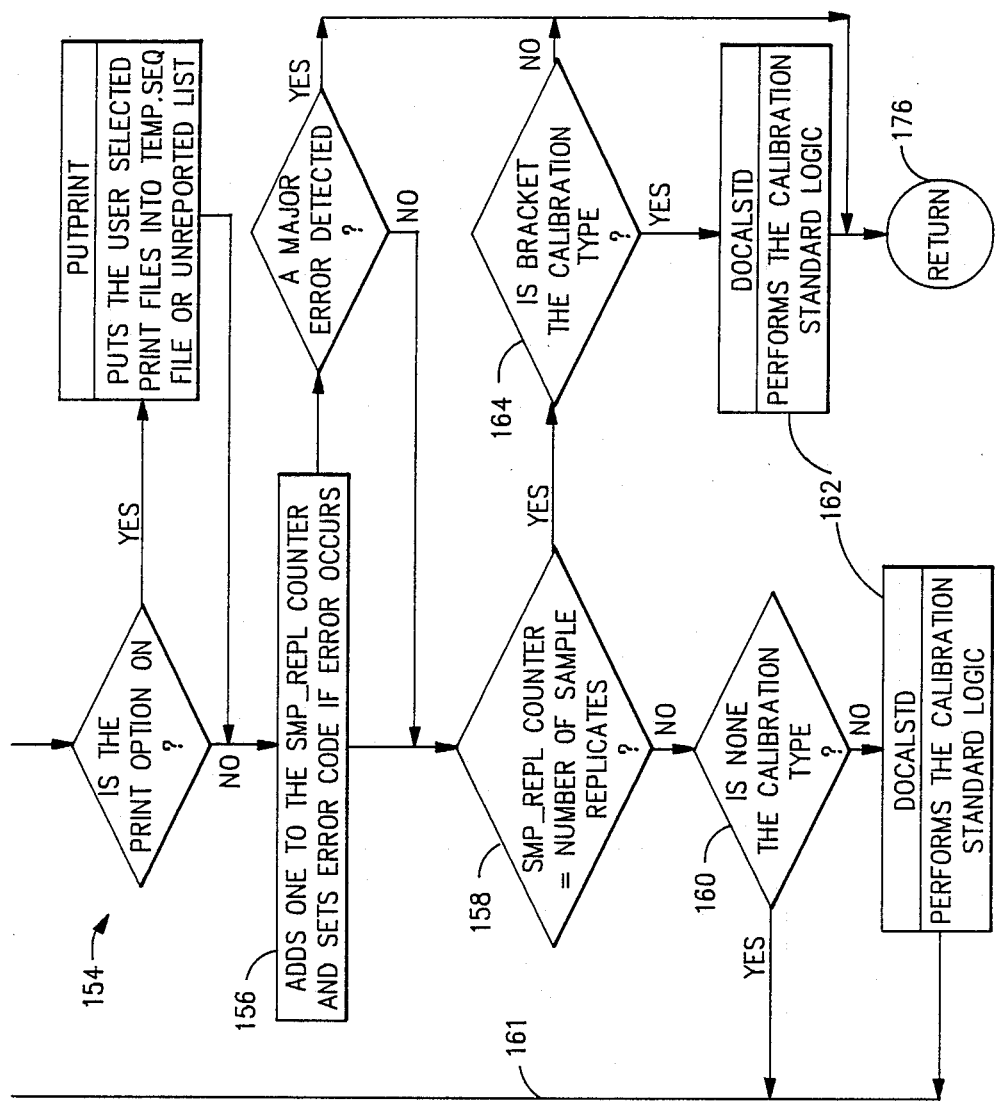
FIG.2.8b
FIG. 2.8a
FIG. 2.8b
FIG.2.8

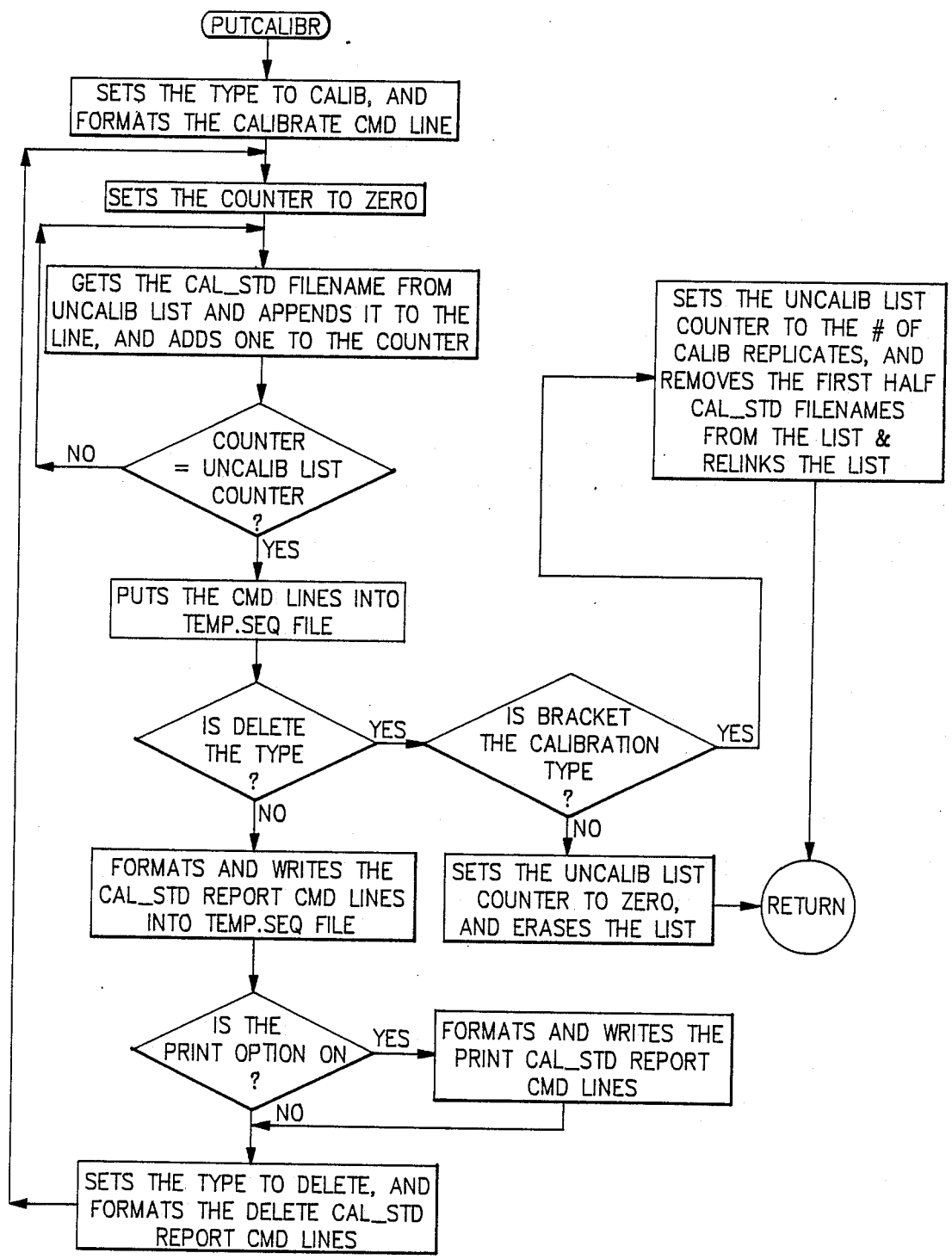
FIG.2.9

CHROMATOGRAPHIC INSTRUMENT WITH COMMAND SEQUENCING

This invention relates generally to the field of chromatographic analysis and particularly to a chromatographic instrument with automated sequencing of a set of commands for sampling specimens in a predetermined order with calibrations interspersed therein.

BACKGROUND OF THE INVENTION

In the broad field of analytical instruments, gas and liquid chromatographs have been used to separate and measure the concentration of the constituents of complex mixtures generally termed samples. In liquid chromatography, a sample is injected into a column having a liquid therein consisting of one or more liquid solvents. A detector at the base of the column detects the presence of the constituents as they appear or elute from the bottom of the column. A plot of the detector output as a function of time, known as a chromatogram, is used by the chromatographer in his analysis of the sample.

For example, it may be desired to know the concentration of a given medication in the blood stream of a patient. A known volume of blood would be entered into a chromatographic column and the constituent parts including the drug fraction would then separate out and be detected. The chromatogram would indicate the concentration of each component. From knowledge of when the medication should separate out, the therapeutic drug level of the medication can be determined. From that, the percentage of medication in the blood can be calculated.

In manually operated instruments a user selects each specimen to be tested one at a time in the desired order, with periodic or intermittent selection of a standard specimen for calibration. The routine is tedious and prone to error, particularly since it is easy for the user to forget to carry out the calibration in the proper order.

Automatic sampling of specimens in a predetermined order with a microprocessor has come into use, such as with a Perkin-Elmer Auto Sampler, solving some of the above-mentioned problems. However state-of-the-art systems still require an operator to place specimen vessels in the receptacle in careful order that matches the selection order of the programmed automatic sampler. A separate calibration specimen must be positioned at periodic positions according to the selected calibration frequency. Flexibility is lacking for making changes in specimens or for preprogramming a procedure change, such as in type of calibration, to occur during a run of tests.

Therefore an object of the present invention is to provide a chromatographic instrument having improved automation of operation.

A more particular object is to provide an improved chromatographic instrument in which an operator places test specimens and a standard specimen in randomly designated locations, and enters procedural information including an ordered list of location information and a preselected calibration frequency, such that the instrument self-generates a set of command instruction lines and effects measurements and computations sequenced according to the ordered list, with at least one calibration command instruction line interspersed therein according to the calibration frequency.

Another object is to provide a chromatographic instrument including a novel command sequence program for generating command instruction lines.

A further object is to provide an improved liquid chromatographic instrument having the above-described features.

SUMMARY OF THE INVENTION

The foregoing and other objects are achieved according to the invention by a chromatographic instrument for automatically testing specimens against a calibration standard specimen. The instrument comprises receptacle means for retaining in random by designated locations a plurality of vessels containing specimen including one or more test specimen and a calibration standard specimen. Sampling means are receptive of specimen location designations for sequentially sampling specimens from selected vessels in the receptacle means. Measuring means are receptive of each sampled specimen and measurement instructions for measuring chosen characteristics of each sampled specimen and generating corresponding measurement information. Output means are receptive of the measurement information for computing and presenting results for each test specimen relative to the standard specimen. A command sequence program generates a set of command instruction lines in sequence. Operational means are receptive of the command instruction lines for effecting instrument operation including instructing the sampling means and the measurement means respectively with the specimen location designations and the measurement instructions according to the sequence generated. Storage means store operator inputed procedural information including an ordered list of location designations for one or more preselected test specimens, a preselected calibration frequency and the measurement instructions.

The command sequence program comprises reading means, command generating means, line counting means and calibration placement means. The reading means read the ordered list to effect a sequential selection of each location designation according to the ordered list. The command generating means are receptive of each sequential selection for generating a corresponding command instruction line containing the location designation and, preferably, the measurement instructions for each selected specimen. The line counting means count the number of command instruction lines generated since a nearest prior calibration command instruction line or initiation of the computer program. The calibration placement means are receptive of the procedural information and responsive to the counting number being equal to the calibration frequency, for generating a next calibration command instruction line containing the location designation and the measurement instructions for the standard specimen The command instruction lines are thereby sequenced according to the ordered list with at least one calibration command instruction line interspersed therein according to the calibration frequency.

BRIEF DESCRIPTION OF THE DRAWINGS

FIGS. 2.1 through 2.9 are integrated flow charts showing an example of the operation of system elements within the command sequence program component of FIG. 1 according to the invention.

DETAILED DESCRIPTION OF THE INVENTION

Figure 1:
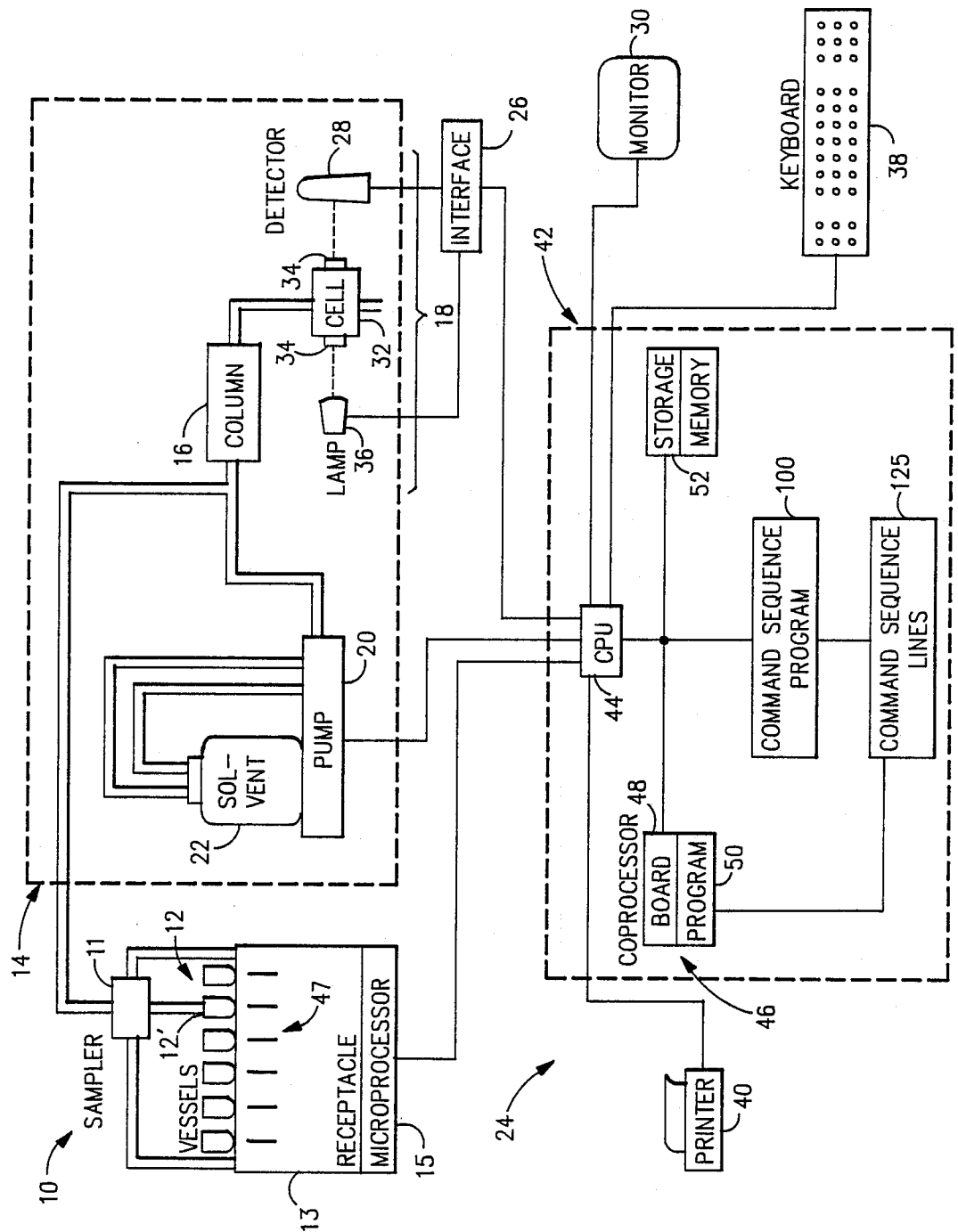
FIG. 1 is a block diagram illustrating the system components of the present invention.

The present invention may be utilized for gas or liquid chromatography. FIG. 1 illustrates the system components of the invention with respect to a liquid chromatographic instrument. The system includes an automatic sampler 10 such as a Perkin-Elmer ISS-100 Auto Sampler or the like for removing samples from vials containing unknown solutions or calibration standards. This sampler has a carriage member 11 which is adapted to take a selected specimen from any vessel 12' of a plurality of specimen vessels 12 in a receptacle 13, and making the specimen available to a measuring means 14 for insertion into a chromatographic column 16. (Vessels are also termed "vials" herein and in the drawings.) A microprocessor 15 controls the carriage 11 and its sampling operation. The column is located before a detector module 18 which in the preferred configuration comprises a Perkin-Elmer Model LC-235 or the like. For each experiment performed by this system, the automatic sampler 10 provides a sample of the solution to be tested to the column and detector.

The system in addition includes a microprocessor controlled pump 20 which, in the preferred embodiment, comprises a Perkin-Elmer Series 620 pump assembly. The microprocessor controlled pump 20 is operative to precisely control the solvent mix from one or more containers 22. The column is used for separating the components of the sample introduced thereto, in the conventional liquid chromatographic method.

The system of FIG. 1 additionally includes an output means comprising a computer module 24. The computer is coupled by a data interface 26 to the auto sampler 10, the detector module 18, and the microprocessor control pump 20. In the preferred embodiment of the present invention, this interface comprises a Perkin-Elmer Single Channel Interface which serves as an analog/digital communication adaptor between the computer module 24 and a detector 28.

The computer module 24, by reason of the programs entered therein, is operative to supervise the activities of the auto sampler 10, the detector module 18, and the microprocessor control pump 20. Indeed, it is through the supervision provided by the computer module 24 that the operator is able to control the system elements to perform a desired set of experiments upon the unknown specimens in the receptacle 13 of the auto sampler 10. In addition, a monitor screen 30 of the computer module 24 provides a means for displaying the results of experiments performed on the samples in the auto sampler 10. The screen 30 also serves as a means to display the system status.

The detector module includes a cell 32 with windows 34 for passing through the liquid flowing under pressure from the column, a source lamp 36 for providing radiation to be transmitted through the liquid in the cell, and the radiation detector 28 for detecting the transmitted radiation as modified by the effects of the injected sample in the solvent mix. The computer 24 conventionally communicates with a keypad or keyboard 38 for operator interface, the monitor 30 for display of information and results, and a printer 40. The computer 42 has a conventional central processing unit 44 (CPU) such as in an IBM personal computer AT ™ or Epson Equity ™ III+ with 640 Mb RAM, 2Mb Rampage ™ board, DOS 3.3 and a hard disk. The computer further includes a master control system 46 for operating the autosampler 10 and processing data information from the detector 28. Master system 46 instructs the auto sampler with specified specimen location designations 47. System 46 comprises, for example, components of a Perkin-Elmer Omega-2 workstation comprising a C-Engine coprocessor board 48 and an associated software program 50 containing routines for computing results, an example being a program taught in U.S. Pat. No. 4,579,663 (Poile) of the present assignee. Results typically are in the form of one or more peak areas characteristic of the sample, or preferably such peak areas ratioed with corresponding peak areas for a calibration standard.

A portion of the memory, designated herein as storage 52, contains operator inputed procedural information on the method of running the instrument and treating the measurement data information. The procedural information (method) at least includes the designated locations of preselected specimen vessels 12 in the receptacle 13 of the autosampler 10, an ordered list of samples in the order selected by an operator to be tested, and a preselected frequency of running a calibration standard. Other procedural information may include sample name, method name, a number of replicates to be run for each sample, an operator selected choice of type of calibration method, type of results to be calculated, how much history of the test is to be saved and presented, method of presenting the results such as printing, and the like.

The specimens include one or more test specimens and, if calibration is desired, at least one calibration standard specimen. Type of calibration may be the "single type", in which a standard specimen is run initially and again periodically according to the preselected calibration frequency. Each test sample is then compared (as by ratio) with the nearest prior calibration data. Another calibration type is the "bracket type" in which the measurement data from pairs of standard tests are averaged, and the results for the test specimens bracketed by the pairs are determined by comparison with the average. In either event appropriate instructions must be provided for saving measurement information for use in computations. Alternately the operator may preselect "none" for calibration.

The computer further includes a command sequence program 100 according to the present invention, in the form of software or firmware. The flowsheets of FIGS. 2.1 to 2.9 illustrate such a program. The more relevant parts of the program are discussed below. The command sequence is conveniently and readily programmed with a conventional program such as "C" generally available through the supplier of the disc operating system utilized with the computer. User input for operating the instrument is conveniently effected via pull-down menus with icons addressed via arrow keys or a mouse, with keyboard entry of information. Typically much of the procedural information will be standardized and retained, and for routine use an operator merely enters the listing of information concerning the samples currently to be tested.

Referring to the master routine 100 in flowsheet FIG. 2.1, once the user has placed the vessels in the receptacle and entered the procedural information including location designations, the program is commenced at 101 by a user selection ANALYSE along with a designation of which test samples (e.g. by number) are to be analyzed. (Other options in box 101 are similar or selfexplanatory). The first portions 102 of the program, including those shown in subroutine CKSMPTBL (FIGS. 2.2 and 2.3), effect initialization and other preliminary matters. Error detection routines here and throughout the program, not detailed herein, crosscheck such items as whether vials in the receptacle match inputed information, sample volumes are sufficient for the tests entered, and the like.

Subroutine CKSMPHMTH 103 is shown in FIGS. 2.4a and 2.4b. After initial steps 104, at 105 a pointer is set to the top of the list of sample specimens to be tested. A conditional statement 106 ascertains whether the method (i.e. procedural information) is the same as previously used; this may be ascertained from a method name change. Initially this answers as "no" (since there was no prior method run yet) and directs the program to subroutine D shown in FIG. 2.5. After further preparation steps 108, if a conditional statement 110 of "none" for calibration type answers "no", thus requiring calibration, the program enters subroutine DOCALIBR 112 shown in FIG. 2.7. At 114 sample information, particularly location of the standard, is obtained by a reading of the ordered list 116. Sufficiency of sample is checked at 118, and another vessel is selected if necessary and available.

An additional subroutine PUTSMPID 120 and the next subroutine PUTSAVE 122 function contiguously as a command generating means to address storage 52 (FIG. 1) for procedural (method) information 124 and to place therefrom into an initial command instruction line the location designation for the standard specimen and the measurement instructions including. This command instruction line is put into a temporary sequence file which eventually is to contain set 125 of command instruction lines.

At 126 instructions for reporting are entered into the instruction line. At 128 an "uncalibrate list" is started for saving calibration measurements for use in computations. A counter 130 is incremented, and a conditional statement 132 checks against an inputed replicate number, and loops to repeat the subroutine to generate additional command instruction lines for the same calibration sample into the temporary sequence file until a count reaches the selected replicate number. Then the system is returned to point 134 in subroutine D (FIG. 2.5), and (after an error check) on to a subroutine PUTCALIBR 136 (FIG. 9) which sets up the instructions into the command instruction line for saving measurements. Thus at least one initial calibration command instruction line is generated, and the system then is returned to point 138 in subroutine D which (after further error checks) returns to point 140 in CKSMPMTH (FIGS. 2.4a) (and more error checks) and thence to subroutine DOSAMPLE 144.

Subroutine DOSAMPLE 144 is shown in FIGS. 2.8. After initially setting a replicate counter 146, it leads to subroutines PUTSMPID 120 and PUTSAVE 122 previously used as described above for the initial calibration, now used for test specimens. These subroutines read the ordered list and other method information and generate a command instruction line for the first test sample in the list, and place it next into the temporary sequence file. This line contains substantially the same type of instructions and information as for the standard. A conditional statement 148 on calibration type directs reporting and save instructions via PUTUNRPT 150 into an "unreported list" for bracket type, or via step 152 such instructions without the unreported list, are put into the command instruction line. Similar instructions 154 for printing are then entered, and replicate counter 156 is incremented and tested 158 for looping.

At program query 160, if "none" is the calibration type, the program loops on 161 until the selected number of replicates is reached. Otherwise the program moves into subroutine DOCALCSTD 162 before looping for a single type calibration check. Also DOCALCSTD 162 is entered after the replicate number is reached and a conditional statement 164 is answered for bracket type calibration.

DOCALCSTD 162 (FIG. 2.6) is a calibration logic subroutine shown in FIG. 2.6. The initial step therein adds one to a sample counter 166 that counts the number of command instruction lines generated since the nearest prior calibration instruction line (or initiation of the program). If a conditional statement 168 reading from the method 124 in storage puts the count at less than the preselected calibration frequency, the remainder of the subroutine is bypassed at 170. Each time the calibration frequency is reached the program is directed to DOCALIBR (FIG. 2.7) and then PUTCALIBR (FIG. 2.9). As explained above these two subroutines function as a calibration placement means to generate a new command instruction line for the calibration standard and place it next into the temporary sequence file. Further steps in DOCALCSTD involve the saving for calibration, and rezeroing 174 of the sample counter, before returning to the loop 161 in DOSAMPLE (FIG. 2.8) or to point 176 in CKSMPMTH (FIG. 2.4a) via the return in DOSAMPLE (FIG. 2.8).

After further error checks 178, CKSMPMTH advances the pointer 180 for the sample list 116 and at 182 queries whether all test sample vials have been processed. If not the program loops back to point 184 to recycle from the method inquiry 106 which is responsive to a change in procedural information, such as a different method name. Any variation procedural information such as calibration or testing details, triggers a return to subroutine D described above, generating a new "initial" calibration command instruction line at this stage with the updated information. Otherwise looping is effected for each successive test sample according to the inputed list, generating for each a corresponding command instruction line. Single calibration type is also queried 186, and if "yes" enters DOCALCSTD 162 (FIG. 2.6) described above.

After all listed samples have been processed, subroutine E (FIG. 2.4b) is entered for error checks, a possible final calibration run (described below), and pulling other usable information into the temporary sequence file. If error checks pass, the program is returned to point 188 in the master routine (FIG. 2.1). WRITESEQ 190 renames the temporary sequence file into a command sequence file consisting of the complete set of command instruction lines 125, and the command sequence program is terminated at 192.

The set 125 of command instruction lines are directed to and utilized by the master system 46 for sequential selection of the test and calibration specimens by the autosampler, directing processing of the specimens selected. Results are outputed via the CPU 44 to the monitor 30 and/or the printer 40 according to reporting instructions from the command instructions lines 125. Thus the ordered set is built by the command sequence program from the ordered list and calibration type and frequency entered by the user. At least one calibration command instruction line ordinarily is interspersed in the set according to the calibration frequency.

If "bracket" is selected for calibration, a final calibration line is included by the program, along with appropriate instructions for saving measurements for computations with an average of the brackets. The final calibration is effected via subroutine E (FIG. 2.4b) to AUTODQ 194. This queries conditions for a final calibration and routes to DOCALIBR and PUTCALIBR which functions as described above. Also, in the event of a method change at point 106 (FIG. 2.4a) causing entry of subroutine D (FIG. 2.5), AUTODQ is similarly entered to effect a final calibration for the prior method group.

If "none" is selected for calibration, none will be included. Although the invention is directed to generating a listing including calibrations, a preferred embodiment includes the operator option to omit calibration, for example for screening runs.

The minimum information in each of the command instruction lines is sample location, the primary purpose of the command sequence being to provide an order of testing with interspersed calibrations. Thus other aspects of the procedural information may, with modified programs, be provided separately in the master program 46 or elsewhere, especially in simplified circumstances where the samples are always run or reported in the same manner.

However, by including procedural information (method) in the instruction lines, there is versatility in allowing for method changes, such as during a run. The command instruction lines actually generated in the program (for example in "C" language) may be relatively simple, consisting of the movement or deletion of temporary or named files in memory or the master program.

It may readily be appreciated that the present invention provides a greatly simplified, less error prone and more versatile instrument over prior art systems with or without computers, in which a user must laboriously place vials including a plurality of calibration standards in proper order in the receptacle and/or match the order with computer entries. Other advantages include a reduction in the number of vials containing standards, thereby reducing the risk of contamination.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

What is claimed is:

1. A chromatographic instrument for automatically testing specimens against a calibration standard specimen, the instrument comprising receptacle means for retaining in randomly designated locations a plurality of vessels containing specimens including one or more test specimens and a calibration standard specimen, automatic sampling means receptive of specimen location designations for sequentially sampling specimens from selected vessels in the receptacle means, measuring means including a chromatography column receptive of each sampled specimen for measuring chosen characteristics of each sampled specimen and generating corresponding measurement information, output means receptive of the measurement information for computing and presenting results for each test specimen relative to the standard specimen, a command sequence program for generating a set of command instruction lines in sequence, operational means receptive of the command instruction lines for effecting instrument operation including instructing the sampling means with the specimen location designations according to the sequence generated, and storage means for storing operator inputed procedural information including an ordered list of location designations for one or more preselected test specimens and a preselected calibration frequency; wherein the command sequence program comprises:

reading means for reading the ordered list to effect a sequential selection of each location designation according to the ordered list;

command generating means receptive of each sequential selection for generating a corresponding command instruction line containing the location designation for each preselected test specimen; line counting means for counting the number of command instruction lines generated since a nearest prior calibration command instruction line or initiation of the command sequence program; and calibration placement means receptive of the procedural information and responsive to the counting number being equal to the calibration frequency, for generating a next calibration command instruction line containing the location designation for the standard specimen, whereby the set of command instruction lines are sequenced according to the ordered list with at least one calibration command instruction line interspersed therein according to the calibration frequency.

2. The instrument according to claim 1 wherein the instrument is a liquid chromatographic instrument.

3. The instrument according to claim 1 wherein the command sequence program further comprises initiation means receptive of the procedural information for generating an initial calibration command instruction line prior to generating any other command instruction line.

4. The instrument according to claim 3 wherein the procedural information is associated with each test sample, and the command sequence program further comprises procedural means responsive to a change in procedural information for a next test sample, for generating a new calibration command instruction line prior to generating a command instruction line for the next test sample.

5. A chromatographic instrument for automatically testing specimens against a calibration standard specimen, the instrument comprising receptacle means for retaining in randomly designated locations a plurality of vessels containing specimens including one or more test specimens and a calibration standard specimen, automatic sampling means receptive of specimen location designations for sequentially sampling specimens from selected vessels in the receptacle means, measuring means including a chromatography column receptive of each sampled specimen and measurement instructions for measuring chosen characteristics of each sampled specimen and generating corresponding measurement information, output means receptive of the measurement information for computing and presenting results for each test specimen relative to the standard specimen, a command sequence program for generating a set of command instruction lines in sequence, operational means receptive of the command instruction lines for effecting instrument operation including instructing the sampling means and the measurement means respectively with the specimen location designations and the measurement instructions according to the sequence generated, and storage means for storing operator inputed procedural information including an ordered list of location designations for one or more preselected test specimens, a preselected calibration frequency and the measurement instructions; wherein the command sequence program comprises:

reading means for reading the ordered list to effect a sequential selection of each location designation according to the ordered list;

command generating means receptive of each sequential selection for generating a corresponding command instruction line containing the location designation and the measurement instructions for each selected specimen;

line counting means for counting the number of command instruction lines generated since a nearest prior calibration command instruction line or initiation of the command sequence program; and calibration placement means receptive of the procedural information and responsive to the counting number being equal to the calibration frequency, for generating a next calibration command instruction line containing the location designation and the measurement instructions for the standard specimen, whereby the set of command instruction lines are sequenced according to the ordered list with at least one calibration command instruction line interspersed therein according to the calibration frequency.

6. The instrument according to claim 5 wherein the instrument is a liquid chromatographic instrument.

7. The instrument according to claim 5 wherein the command sequence program further comprises initiation means receptive of the procedural information for generating an initial calibration command instruction line prior to generating any other command instruction line.

8. The instrument according to claim 7 wherein the procedural information is associated with each test sample, and the command sequence program further comprises procedural means responsive to a change in procedural information for a next test sample, for generating a new calibration command instruction line prior to generating a command instruction line for the next test sample.

9. The instrument according to claim 5 wherein the procedural information further includes a replicate number representing a preselected number of repetitions of sampling each specimen, and the command generating means includes replicate means responsive to the replicate number for generating a replicate number of command instruction lines for each preselected specimen.

10. The instrument according to claim 5 wherein the measurement information includes reporting instructions for placement into the command instruction lines, and the output means is receptive of the reporting instructions from the command instruction lines for computing and presenting the results.

11. The instrument according to claim 10 wherein the reporting instructions include single type calibration instructions for computing the results of each test specimen relative to the standard specimen as measured according to a prior calibration command instruction line nearest to the command instruction line of said each test specimen, the single type instructions including save instructions for saving each prior calibration measurement in preparation for computing said results.

12. The instrument according to claim 10 wherein the reporting instructions include bracket type calibration instructions for computing the results of each test specimen relative to the standard specimen as measured according to an average of a nearest prior calibration measurement and a nearest subsequent calibration measurement, the nearest prior measurement and the nearest subsequent measurement being such as to sequentially bracket corresponding test specimen measurements, the bracket type instruction including first save instructions for saving each prior calibration measurement in preparation for computing said average, and further including second save instructions for saving the bracketed in preparation for computing said results.

13. The instrument according to claim 10 wherein:

the reporting instructions include single type calibration instructions for computing the results of each test specimen relative to the standard specimen as measured according to a prior calibration command instruction line nearest to the command instruction line of said each test specimen, the single type instructions including save instructions for saving each prior calibration measurement in preparation for computing said results;

the reporting instructions further include bracket type calibration instructions for computing the results of each test specimen relative to the standard specimen as measured according to an average of a nearest prior calibration measurement and a nearest subsequent calibration measurement, the nearest prior measurement and the nearest subsequent measurement being such as to sequentially bracket corresponding test specimen measurements, the bracket type instructions including first save instructions for saving each prior calibration measurement in preparation for computing said average, and further including second save instructions for saving the bracketed measurements in preparation for computing said results relative to said average;

the procedural information further includes an operator selected choice between the single type calibration and the bracket type calibration; and the command generating means further comprises selection means receptive of the selected choice for placing into a corresponding command instruction line the correspondingly selected single or bracket type instructions.

14. The instrument according to claim 13 wherein the procedural information further includes an operator selected choice among the single type calibration, the bracket type calibration and a no calibration, and the placing means further comprises omission means receptive of the choice of no calibration for omission of any calibration command instruction line in the set of command instruction lines.

* * * * *